United States Patent [19]

Sagstetter et al.

[11] Patent Number: 4,664,653
[45] Date of Patent: May 12, 1987

[54] MANUALLY OPERATED REUSABLE INJECTION APPARATUS

[76] Inventors: William E. Sagstetter, 2217 Grove St., Denver, Colo. 80211; Alan A. Wanderer, 3601 S. Pennsylvania, Englewood, Colo. 80110

[21] Appl. No.: 832,084

[22] Filed: Feb. 24, 1986

[51] Int. Cl.4 ............................................. A61M 5/00
[52] U.S. Cl. .................................. 604/197; 604/194; 604/192
[58] Field of Search ............... 604/187, 192, 194, 197, 604/90, 139

[56] References Cited

U.S. PATENT DOCUMENTS

| | | | |
|---|---|---|---|
| 3,721,241 | 3/1973 | Klohr et al. | 604/192 |
| 3,742,948 | 7/1973 | Post et al. | 604/197 |
| 3,890,971 | 6/1975 | Leeson et al. | 604/197 |
| 3,943,927 | 3/1976 | Norgren | 604/197 |
| 4,394,863 | 7/1983 | Bartner | 604/90 |
| 4,592,745 | 6/1986 | Rex et al. | 604/192 |

Primary Examiner—Gene B. Kartchner

[57] ABSTRACT

One step manually activated injection apparatus capable of injecting multiple pre-measured doses of liquid medicaments without visibility of needle. It is composed of cylindrical housing unit with small aperture at bottom and removeable manual plunger unit at the top, and within housing unit there is a syringe unit composed of a piston, ampule with pre-measured liquid medicament, needle covered with sterile sheath and clip apparatus attached onto the ampule. The injection apparatus is placed in ready position by contacting the bottom of housing unit against a skin surface. One forward manual push on manual plunger unit performs two distinct functions. First, the manual plunger unit engages the clip apparatus attached to syringe ampule, permitting forward movement of syringe unit within housing unit, allowing needle to pierce sheath and pass externally through aperture of housing unit without visibility into the skin. Secondly, a continuous forward push on manual plunger unit allows clip apparatus to move into reduced diameter transitions in housing unit, forcing clips internally to contact onto ampule, permitting manual plunger unit to disengage from clip apparatus and move forward exerting pressure on syringe piston, which pushes liquid medicament through needle into the skin. After injection of liquid medicament, radial pressure exerted by clip apparatus against internal diameter of manual plunger unit permits removal of syringe unit (i.e. clip apparatus, syringe piston, needle and sheath) simply by pulling removeable manual plunger unit from housing unit. This allows ad-finitum exchange of syringe unit refills into cylindrical housing unit for subsequent premeasured liquid medicament injections.

4 Claims, 8 Drawing Figures

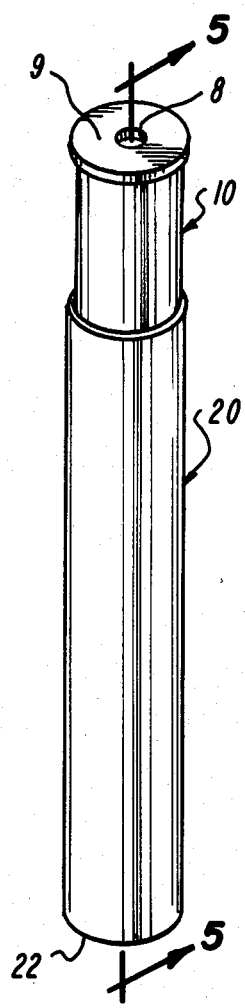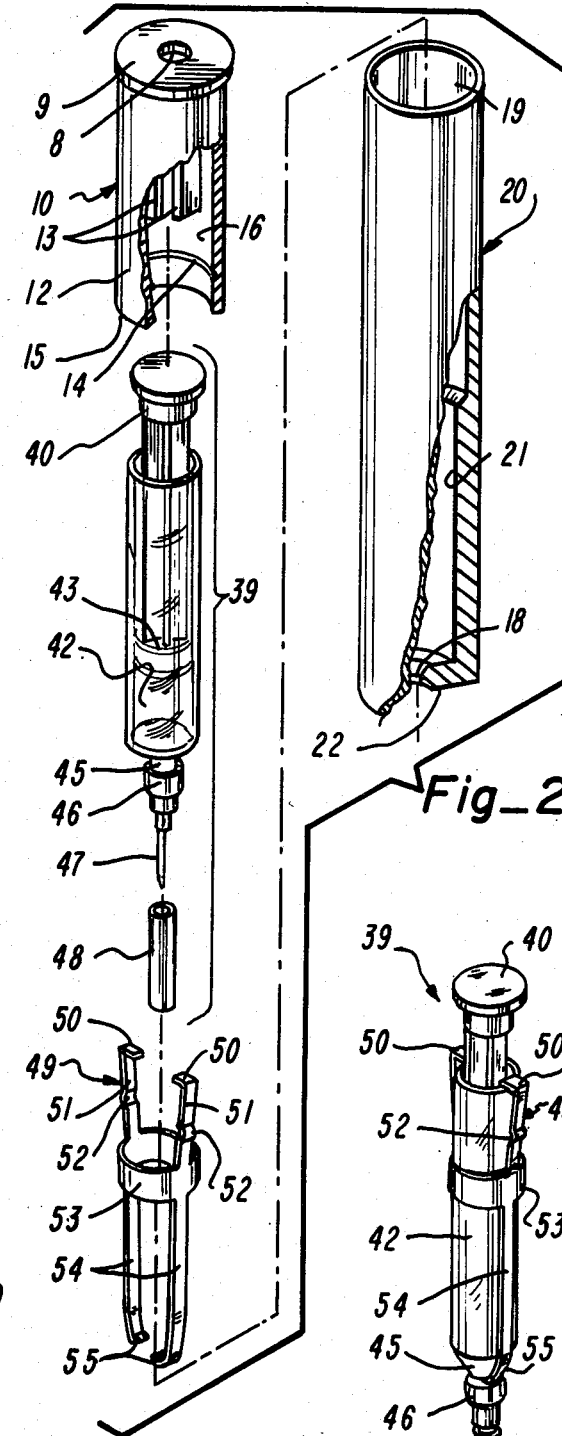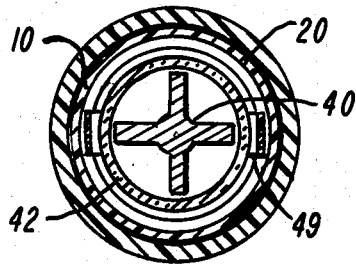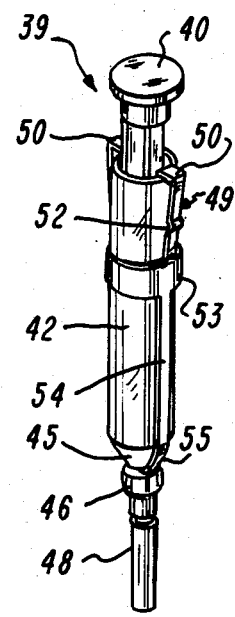
U.S. Patent  May 12, 1987  Sheet 1 of 2  4,664,653
Fig_1
Fig_2
Fig_6
Fig_3

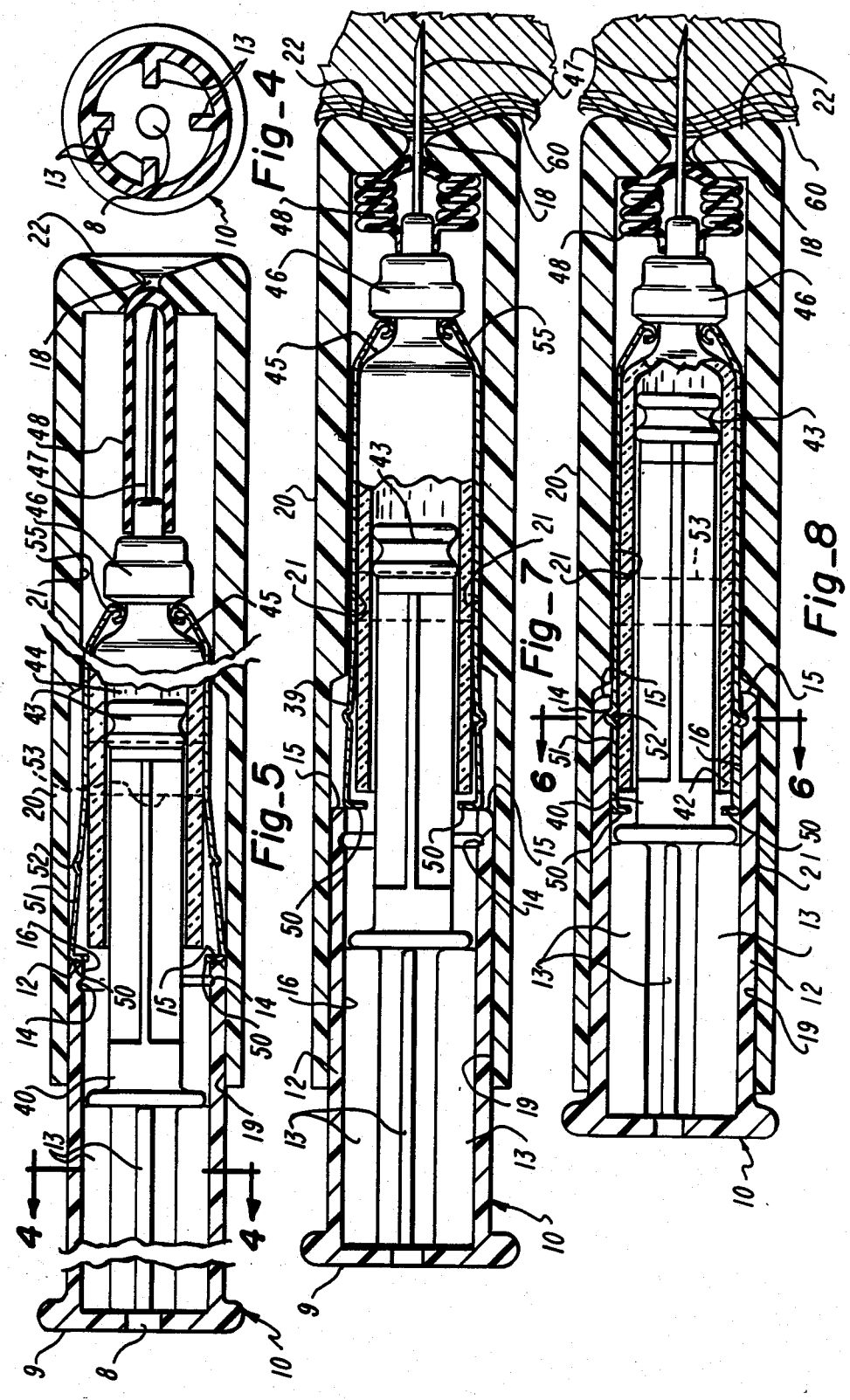

MANUALLY OPERATED REUSABLE INJECTION APPARATUS

BACKGROUND OF THE INVENTION

This invention relates to a manually operated injection apparatus that permits medically untrained individuals to easily self-administer liquid medicaments, and more particularly relates to an injection apparatus that is capable of rapid, easily mastered multiple refills of medicament which may be required for treatment of medical emergencies. For example, this device can be used with adrenalin for several life-threatening medical emergencies such as: bee sting reactions, immediate allergic-like reactions to ingestants such as drugs, foods, food additives (metabisulfite, monosodium glutamate, yellow tartrazine coloring dyes), acute hives with associated shock-like symptoms, acute bronchial asthma, etc. More than a single dose of adrenalin can be required to treat and reverse these life-threatening situations. These adrenalin injection devices can be particularly life-saving for individuals when immediate medical attention is not available.

There are several problems inherent in existing self-administration injection designs. These include (1) complicated designs which are difficult to understand and use. In addition, certain designs exhibit needle visibility which can cause undue fear reactions in individuals who must self-administer life-saving drugs. (2) expensive retail costs reducing consumer availability. This problem is reflective of design and manufacturing complexity of the injection device (3) according to its instructions, one device is incapabile of operating when the injection device is cold, which will cause time delays in treating medical emergencies. (4) lack of or difficult refilling capabilities needed for treatment of medical emergencies that do not respond to a single dose of medicament.

The following patent references were selected from a search through the U.S. Patent and Trademark Office as the closest patented art in the field: Leiter, U.S. Pat. No. 159,192; Morton, U.S. Pat. No. 1,767,304; Lockhart, U.S. Pat. No. 2,408,323; Maynes, U.S. Pat. No. 2,472,116; Smith, U.S. Pat. No. 2,475,061; Tydings, U.S. Pat. No. 2,489,600; Harnisch, U.S. Pat. No. 2,671,448; Huber, U.S. Pat. No. 2,688,965; Jensen, U.S. Pat. No. 2,704,073; Uytenbogaart, U.S. Pat. No. 2,752,918; Rockwell, U.S. Pat. No. 2,856,924; Wilburn, U.S. Pat. No. 2,860,635; Craig, U.S. Pat. No. 2,925,083; Roehr, U.S. Pat. No. 3,008,570, Hershberg, U.S. Pat. No. 3,572,336; Sarnoff, U.S. Pat. No. 3,882,863; Leeson, U.S. Pat. No. 3,890,971; Rimbaud, U.S. Pat. No. 3,930,499; Norgren, U.S. Pat. No. 3,943,927.

The following patent designs and commercially available devices exhibit some of the aforementioned limitations.

U.S. Pat. No. 2,475,061 issued to A. E. Smith (1) is a complicated manual operated design which requires first unthreading and removing a skirt and plunger from housing sleeve, then manually assisting ampule through an introduction slot, and finally replacing and rethreading skirt with plunger onto housing sleeve and (2) by patent description requires that the needle be visible prior to the injection of medicament into the skin.

U.S. Pat. No. 2,489,600 issued to Tydings and Tash is also a complicated manually operated design which requires first removal of plunger and skirt and insertion of ampule and needle combination into housing. The needle must be pushed through ampule plug and by patent description the needle becomes visible before it is injected into the skin. Thereafter there is a complicated method to refill since it is necessary to inject medicament into the existing ampule in housing with an auxiliary syringe and needle device.

One commercially available kit with no listed patent number (ANA Kit), has needle visibility and a complicated three stage plunger design that can be confusing. The first push of the plunger which is designed to remove excess air and liquid can be confused with the second stage push which actually administers a full dose of medicament. Additionally, the second dose of medicament can only be used in the same time frame, as the needle has been used once and would thus be contaminated for use at a later time period.

A manually-activated injection device disclosed in U.S. Pat. No. 3,943,927 issued to Norgren: (1) uses cross arms that move outwardly from center of housing. The net result is a design requirement for a larger diameter housing, making it potentially awkward for manual handling, and (2) does not exhibit multi-dose capabilities because once the medicationis pushed through the needle that punctures relief area, there is no provision to permit delivery of a second dose of medicament or to refill the housing with a second refill cartridge.

Another commercially available design disclosed in U.S. Pat. No. 3,882,863 issued to Sarnoff and Catkins is: (1) a complicated coiled-spring release mechanism that is expensive to produce, (2) potentially dangerous to the user if the powerful coiled-spring is released through a defective plastic housing, (3) not be operated if it is refrigerated or stored in cold conditions, which may cause serious time delays in delivery of an emergency medicament since the device should only be used after it equilibrates to a temperature between 59°–86° F., (4) not capable of multidose administration since once the coiled-spring mechanism has been actuated, there is no provision for delivery of a second dose of medicament.

SUMMARY OF THE INVENTION

This invention is a simple easily refilled manual-operated injection apparatus comprised of a manual plunger unit, and a housing unit in which is inserted a syringe unit with attached clip apparatus.

An object of this invention is to provide a design that is simple to understand and utilize. This is accomplished by a design that uses one continuous manual movement to perform two successive functions. One push on manual plunger unit engages clip apparatus attached to syringe unit, permitting forward movement of syringe unit inside housing unit, allowing needle to move forward through sheath and aperture of housing unit into the skin without needle visibility. Continuous push on the manual plunger unit moves clip apparatus forward into diameter transition in housing unit, causing clip apparatus to contact the ampule surface and thus disengage from manual plunger unit. This permits manual plunger unit to engage piston in syringe unit, thus pushing medicament through needle into skin.

Another object of this invention is to provide efficient use of manual forces by inward movement of clip apparatus towards central vertical axis of housing, such that the diameter of housing unit can be reduced, creating a design that has a small diameter, which is easier to manipulate and store.

An additional object of the present invention is the provision of a simple design which would be inexpensive to manufacture. This design only requires a manual plunger unit, a housing unit with internal diameter transitions, a syringe unit with liquid medicament and a clip apparatus attached to the ampule part of the syringe unit. This overall design simplicity could permit less expensive manufacturing and retail costs compared to complicated manual or coiled spring-loaded devices.

Another object is to provide a safe delivery system that does not utilize powerful coiled springs, which potentially can cause injury to the user if the coiled spring is accidentally released through a defective plastic housing.

A further object is to allow for immediate usage of the injection device after refrigeration or in cold climatic conditions. One expensive commercially available coiled spring-loaded injection device indicates in its instructions that it cannot be refrigerated or cooled since it must be stored between 59° to 86° F.

An important object is to provide for easy ad-finitum refill capabilities. A single pulling motion on the removeable manual plunger unit will unload attached syringe unit as a result of outward forces of clip apparatus exerted against the internal diameter of the manual plunger unit. A refill syringe unit can then be inserted into the empty housing unit.

Other objectives and advantages of this invention will become apparent more fully from the following description and accompanying drawing illustrating the device.

BRIEF DESCRIPTION OF THE DRAWINGS

FIG. 1 is a perspective view illustrating the injection apparatus consisting of housing unit and manual plunger unit in the ready position.

FIG. 2 is an exploded view of the injection apparatus illustrating manual plunger unit, housing unit, syringe unit and clip apparatus.

FIG. 3 is a perspective view of the clip apparatus attached to the syringe unit.

FIG. 4 is a cross-sectional view of FIG. 5 at line 4—4 illustrating ribs inside the manual plunger unit.

FIG. 5 is a longitudinal broken away view of FIG. 1 taken along line 5—5, illustrating the injection apparatus in ready position.

FIG. 6 is a crross-sectional view of FIG. 8 at line 6—6 illustrating L-shaped members of clip apparatus contacting ampule and the locking of internal annular groove in wall of manual plunger with lateral protrusion of clip apparatus.

FIG. 7 is a view similar to FIG. 5 illustrating the forward movement of the syringe unit inside the housing unit with the needle puncturing the skin.

FIG. 8 is a view similar to FIG. 7 illustrating the full compression of the manual plunger unit after expressing medicament into the skin. The injection apparatus is now in position for extraction of entire syringe unit with clip apparatus from the housing.

DETAILED DESCRIPTION OF THE INVENTION

Referring to the drawings, an injection apparatus is illustrated in FIG. 2., which comprises the manual plunger unit 10, housing unit 20, syringe unit 39 and clip apparatus 49. The manual plunger unit 10 includes top of plunger 9, air vent 8, internal ribs 13, cylindrical wall 12, internal surface 16 of wall 12, bottom of plunger 15, and internal annular groove 14. The housing unit 20 is composed of housing opening 19, diameter transitions 21, and aperture 18 at bottom of housing 22. The syringe unit 39 includes plastic piston 40, ampule (containing liquid medicament) 42, rubber piston 43, tapered part of ampule 45, hub 46, needle 47, and rubber sheath 48. The clip apparatus 49 includes a pair of L-shaped members 50, leaf springs 51, lateral protrusions 52, vertical struts 54, tapered sections 55 and collar 53.

Referring to FIG. 3, the clip apparatus 49 slip fits onto the ampule 42 of the syringe unit 39. The clip apparatus 49 is secured to the ampule 42 by the collar 53 and tapered portion 55 onto the tapered part of the ampule 45.

Referring to FIG. 5, the cylindrical wall 12 of bottom of plunger 15 contacts the L-shaped member 50 of the clip apparatus 49. The injection apparatus in ready position FIG. 5, reveals that the leaf springs 51 are located above the diameter transitions 21 of the housing unit 20.

Referring to FIG. 7 with the bottom of the housing 22 pushed against the skin surface 60, manual pressure applied to top of plunger 9 pushes bottom of plunger 15 against L-shaped members 50, moving syringe unit 39 forward in housing unit 20, forcing needle 47 through rubber sheath 48 into skin surface 60. Referring to FIG. 8, the clip apparatus 49 moves forward into the diameter transitions 21 of the housing unit 20, forcing the leaf springs 51 to contact onto the ampule 42, disengaging the L-shaped members 50 from the bottom of plunger 15, allowing the internal ribs 13 in FIG. 4 to contact the plastic piston 40. This force moves the plastic piston 40 forward, causing the attached rubber piston 43 to expel the liquid medicament through the needle 47 into the skin.

Referring to FIG. 8, radial pressure of the leaf springs 51 against the internal surface of wall 16 of manual plunger unit 10 primarily secures the syringe unit 39 to the manual plunger unit 10. FIG. 6 reveals an additional locking mechanism provided by the lateral protrusion 52 of the clip apparatus 49 which locks inside the internal annular groove 14 of the internal surface of wall 16 of the manual plunger unit 10. Removal of manual plunger unit 10 from housing unit 20 removes syringe unit 39 with attached clip apparatus 49. This allows the empty housing unit 20 to be refilled with a new syringe unit 39 with clip apparatus 49 for injection of second dose of medicament.

We claim:

1. A manually operated refillable injection apparatus comprising:
    a housing unit having diameter transition means and aperture means, said aperture means located at a distal end of said housing unit,
    a syringe unit operatively engagable within and removable from said housing unit comprising; an ampule containing liquid medicament, a piston, a needle, and a sterile protective sheath,
    a manual plunger unit operatively engagable with and removable from the proximal end of said housing unit, said manual plunger having internal rib means contacting said piston,
    a clip apparatus fitted to said ampule, said clip apparatus having L-shaped members which engage a distal end of said manual plunger unit such that, a manual pushing force applied to a proximal end of said plunger unit moves said syringe unit distally within said housing unit pushing said needle into the skin, said diameter transition means providing guide means for guiding said L-shaped members radially inwardly to contact said ampule as said manual plunger unit is pushed thereby disengaging said L-shaped members from the distal end of said manual plunger unit and whereupon, continued pushing of said manual plunger unit causes said internal rib means to push said piston in the distal direction and force liquid medicament through said needle into the skin, said sterile protective sheath having a closed distal end and a proximal end, said proximal end permanently and sealingly engaging said needle thereby preventing contamination of said needle, said sheath being piercable by said needle when said manual plunger unit is pushed into said housing unit, thereby allowing the needle to enter the skin of the patient directly after passing through said sheath and said aperture, said sheath remaining attached to and being removed with said syringe unit whereby, a plurality of syringe units may be used within the housing unit without compromizing the sterility of the needles of said syringe units.

2. A manually operated refillable injection apparatus comprising:

a housing unit having diameter transition means and aperture means, said aperture means located at a distal end of said housing unit, a syringe unit operatively engagable within and removable from said housing unit comprising; an ampule containing liquid medicament, a piston, a needle and a sterile protective sheath, a manual plunger unit operatively engagable with and removable from the proximal end of said housing unit, said manual plunger having internal rib means contacting said piston, a clip apparatus fitted to said ampule, said clip apparatus having L-shaped members which engage a distal end of said manual plunger unit such that, a manual pushing force applied to a proximal end of said plunger unit moves said syringe unit distally within said housing unit pushing said needle into the skin, said diameter transition means providing guide means for guiding said L-shaped members radially inwardly to contact said ampule as said manual plunger unit is pushed thereby disengaging said L-shaped members from the distal end of said manual plunger unit and whereupon, continued pushing of said manual plunger unit causes the said internal rib means to push said piston in the distal direction and force liquid medicament through said needle into the skin, said clip apparatus providing primary and secondary locking means within said manual plunger unit for locking said clip apparatus to said manual plunger unit, such that said syringe unit with said clip apparatus can be unloaded from said housing unit by disengaging said manual plunger unit from said housing unit.

3. The invention of claim 1 or 2 wherein, said clip apparatus further comprises a collar and tappered section which secures said clip apparatus to said syringe unit.

4. The invention of claim 1 or 2 wherein, said L-shaped members are connected to said clip apparatus by leaf spring means whereby, said leaf spring means are moved inward towards a central vertical axis of said housing unit by said guiding means.

* * * * *